United States Patent [19]

Kummerfeld

[11] Patent Number: 5,479,958

[45] Date of Patent: Jan. 2, 1996

[54] SUPPLY UNIT FOR MEDICAL TREATMENT INSTRUMENTS

[75] Inventor: Ryszard Kummerfeld, Travemünde, Germany

[73] Assignee: Dragerwerk AG, Lubeck, Germany

[21] Appl. No.: 406,503

[22] Filed: Mar. 20, 1995

[30] Foreign Application Priority Data

May 11, 1994 [DE] Germany .......................... 44 16 618.4

[51] Int. Cl.[6] .................................................. A01G 25/09
[52] U.S. Cl. ...................... 137/357; 137/355.16; 248/49; 248/58
[58] Field of Search .............................. 137/355.16, 356, 137/357, 343; 248/49, 58

[56] References Cited

U.S. PATENT DOCUMENTS

| | | | |
|---|---|---|---|
| 1,395,616 | 11/1921 | Stroberger | 137/357 |
| 2,021,544 | 11/1935 | Crown | 137/234.6 |
| 2,935,080 | 5/1960 | Klimek | 137/355.16 |
| 4,380,244 | 4/1983 | Caudill et al. | 137/355.16 |
| 4,526,090 | 7/1985 | Maier | 137/355.16 |
| 5,149,017 | 9/1992 | McEntire et al. | 248/49 |
| 5,344,084 | 9/1994 | Andrews et al. | 137/355.16 |
| 5,413,135 | 5/1995 | Poole | 137/357 |

FOREIGN PATENT DOCUMENTS

| | | | |
|---|---|---|---|
| 215212 | 7/1986 | European Pat. Off. | A61G 12/00 |
| 8304407 | 2/1983 | Germany | A61B 19/00 |

*Primary Examiner*—A. Michael Chambers
*Attorney, Agent, or Firm*—McGlew and Tuttle

[57] ABSTRACT

A supply unit with a structural-tubing-type supply beam fastened to a ceiling with supply lines and with a carriage displaceable along the supply beam with a support device for medical treatment instruments. The line routing of the supply lines is extensively hidden, without the displaceability of the carriage being reduced. The supply lines are guided freely displaceably in the form of a loop within the supply beam, and they are deflected via a tube guide to the support device, and that partial lengths $L_1$ and $L_2$ of the supply lines within the supply beam are selected to be such that they correspond to a predetermined movement of the carriage.

10 Claims, 4 Drawing Sheets

SUPPLY UNIT FOR MEDICAL TREATMENT INSTRUMENTS

FIELD OF THE INVENTION

The present invention pertains to a supply unit for medical treatment instruments with a structural-tubing-type supply beam, which is fastened to a ceiling and contains electrical and medical gas supply lines, with tracks extending longitudinally on the supply beam for a carriage, and with a support device arranged on the carriage.

BACKGROUND OF THE INVENTION

A supply unit of the type described above has become known from EP-A 215,212. A track, which extends along the supply beam, consists of two parallel rails. On the track a slide with a support device for medical treatment instruments is guided. The track is arranged on the underside of a structural-tubing-type supply beam fastened to a ceiling. By displacing the slide along the track, the support device can be brought into a favorable position, e.g., to a patient bed. Supply connections, e.g., electric outlets, and couplings for medical gases, which are used for energy supply for the treatment instruments located on the support device, are arranged on the longitudinally extending side parts of the supply beam bent off toward the ceiling. The energy supply lines arriving from the treatment instruments are plugged into the supply connections on the supply beam.

The disadvantage of the prior-art supply unit is the fact that the displacement of the slide on the track may be hindered by excessively short energy supply lines, and these energy supply lines must be replaced with longer ones when necessary. This makes handling difficult during routine clinical operation. On the other hand, excessively long energy supply lines are also undesirable, because this makes the arrangement of the lines confusing and unwieldy.

A support device for medical instruments, which can be positioned by means of a carriage which is longitudinally displaceable on a track, has become known from German Utility Model No. DE-GM 83,04,407. Electrical supply lines are guided to the supply connections on the support device by means of a cable trolley, which is fastened to the track and is equally displaceable, so that the energy supply lines of the medical instruments can be directly connected to supply connections on the support device.

The disadvantage of this prior-art device is the fact that the unsupported line routing via the cable trolley is not desirable for reasons of case of cleaning and because of the appearance, and that it is suitable only for lightweight supply lines, e.g., electrical cables, but not for a bundle of tubes carrying medical gases.

SUMMARY AND OBJECTS OF THE INVENTION

The primary object of the present invention is to improve a supply unit of the type described above such that the treatment instruments can be supplied with energy from the support device, and the supply lines leading to the support device are extensively guided as hidden supply lines, without limiting the displaceability of the support device along the supply beam.

According to the present invention the supply lines are accommodated within the supply beam in the form of a loop with the partial lengths $L_1$ and $L_2$. The supply lines are deflected from the supply beam via a tube guide to the support device. The sum of the partial lengths $L_1$ and $L_2$ of the freely displaceable supply lines within the supply beam is selected to be such that it corresponds at least to a predetermined movement of the carriage.

The advantage of the present invention is essentially the fact that due to the displaceable, loop-like arrangement of the supply lines within the supply beam, the supply lines for the user are guided extensively as hidden supply lines, and, on the other hand, the displaceability of the support device located on the carriage is not hindered. In addition, the possibility of cleaning the supply unit is markedly improved by the line routing according to the present invention.

The supply lines are advantageously accommodated within the supply beam such that they lie on its underside.

The individual supply lines, which may consist of lines carrying medical gases and electrical lines, are advantageously held together with a tube-like jacket. The tube-like jacket may be applied in pieces, or it extends over the entire length of the supply lines within the supply beam.

The jacket preferably consists of individual, box-like segments, which are connected to a so-called cable chain by means of hinges.

The tube guide is advantageously designed as a deflecting plate, which is connected to the support device and extends along a sectional front side or a sectional rear side of the supply beam. The sectional front side and the sectional rear side are bent off at an angle to the underside of the supply beam, and they extend along the tracks, on which the carriage with the support device is displaceable. The deflecting plate is preferably guided to the top edge of the sectional front side or the sectional rear side to guarantee good deflection of the supply lines from the interior of the supply beam to the support device. The deflecting plate may also be bent over the top edge of the respective sectional side into the interior of the supply beam to protect the supply lines from damage.

The deflecting plate is preferably arranged on the sectional rear side not visible to the user, and the height $h_1$ of the sectional front side and the height $h_2$ of the sectional rear side are selected to be such that $h_2$ is smaller than $h_1$. If the height $h_2$ is selected to be such that it is smaller than $h_1$ at least by the thickness of the supply lines, the line routing is completely hidden to the user, whose view is directed toward the sectional front side.

The tube guide is advantageously designed as a slot-like opening extending along the tracks, which extends on the underside of the supply beam. Through the opening, the supply lines can be directly deflected from the interior of the supply beam to the support device.

The supply connections are preferably arranged in the immediate vicinity of the treatment instruments located on the support device, and it is possible to limit the length of the individual energy supply lines between the supply connections and the treatment instruments to a minimum, as a result of which the clarity of the layout of the line routing is substantially increased.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DETAILED DESCRIPTION OF THE PREFERRED EMBODIMENT

Figure 1:
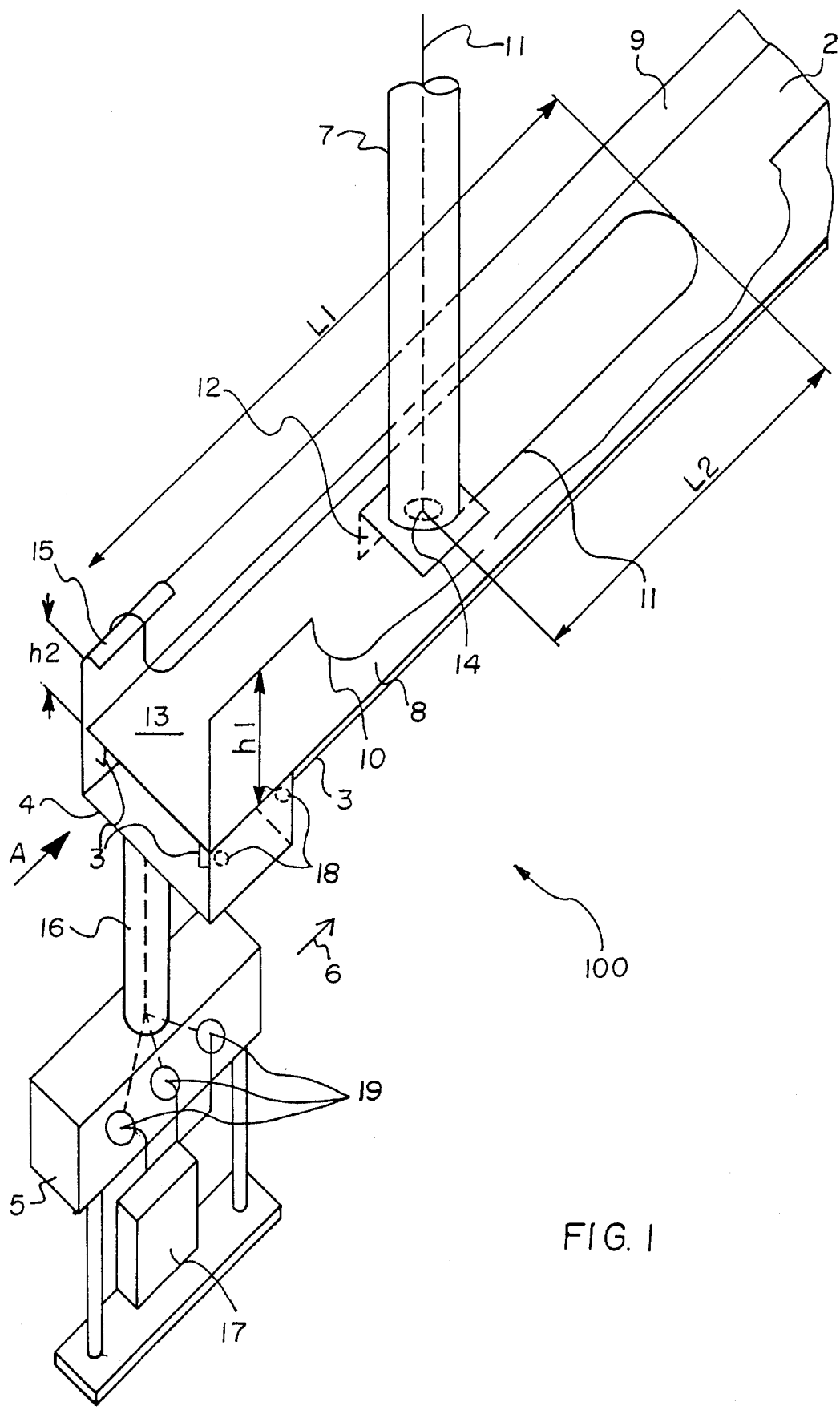
FIG. 1 is a perspective view of a first embodiment of a supply unit according to the invention.

FIG. 1 shows a perspective view of a first supply unit 100, with a supply beam 2 and with tracks 3 on the underside 13 of the supply beam 2. On the tracks 3 a carriage 4 with a support device 5 is guided longitudinally displaceably. The direction of displacement is indicated by an arrow 6. In the position shown in FIG. 1, the carriage 4 is at the left-hand stop of the supply beam 2. The supply beam 2 is fastened to the ceiling by means of support sections 7. Of the support sections 7, FIG. 1 shows only the frontmost support section 7. The supply beam 2 consists of a U-shaped section with a sectional front side 8 of the height $h_1$ and of a sectional rear side 9 of the height $h_2$. For the sake of greater clarity, the sectional front side 8 is cut open along a cutting line 10. The support section 7, which is designed as a structural tubing for accommodating supply lines 11, is fastened by means of an angle 12 to the supply beam 2, which is welded to the sectional front side 8 and to the underside 13. In the area of the connection point between the angle 12 and the support section 7, the angle 12 has a hole 14, through which the supply lines 11 can be introduced into the trough-like section of the supply beam 2. The supply lines 11 are represented in FIG. 1 only schematically by a broken line; they normally consist of a bundle of lines carrying medical lines and electrical lines (see FIG. 5). The supply lines 11 lie on the underside 13 of the supply beam in the form of a loop, and they are deflected as a tube guide in the direction of the support device 5 by means of a deflecting plate 15, which is rigidly connected to the carriage 4 and extends in parallel to the sectional rear side 9. The support device is fastened to the carriage 4 by means of a pipe 16. Supply connections 19, which are connected to the supply lines 11 and are used to supply a medical treatment instrument 17 located on the support device 5 with energy, are arranged on the support device 5. The carriage is displaceable on the tracks 13 by means of rollers 18.

When the carriage 4 is displaced in the direction of the arrow 6, the partial lengths $L_1$ and $L_2$ of the freely displaceable supply lines 11 within the supply beam 2 change, i.e., $L_2$ increases as $L_1$ decreases. As a result, it is always possible to feed the supply lines 11 to the instantaneous position of the carriage 4. The overall length $L_1 + L_2$ of the supply lines 11 within the supply beam 2 is determined by the movement which the carriage 4 is to perform. To keep the lines along the deflecting plate 15 hidden to a user standing in front of the treatment instrument 17 looking toward the sectional front side 8, the profile of the supply beam 2 is designed such that the height $h_1$ of the sectional front side 8 is greater than the height $h_2$ of the sectional rear side 9.

Figure 2:
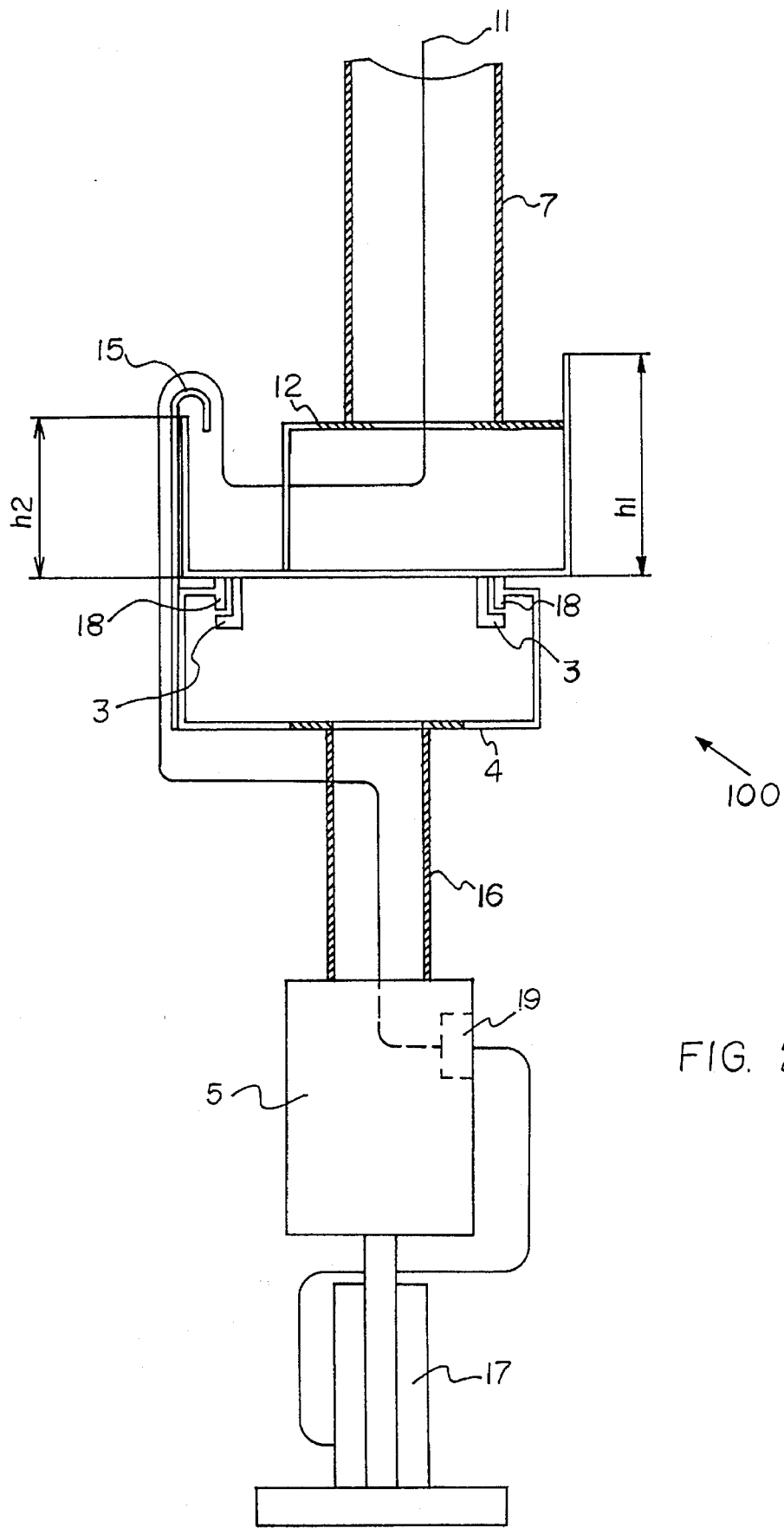
FIG. 2 is a side view of the supply unit according to FIG. 1 in the viewing direction "A"

FIG. 2 shows a side view of the first supply unit 100 in the viewing direction "A" according to FIG. 1. Identical components are designated by the same reference numbers as in FIG. 1. For the sake of greater clarity, the supply lines 11 are shown at a spaced location from the deflecting plate 15.

Figure 3:
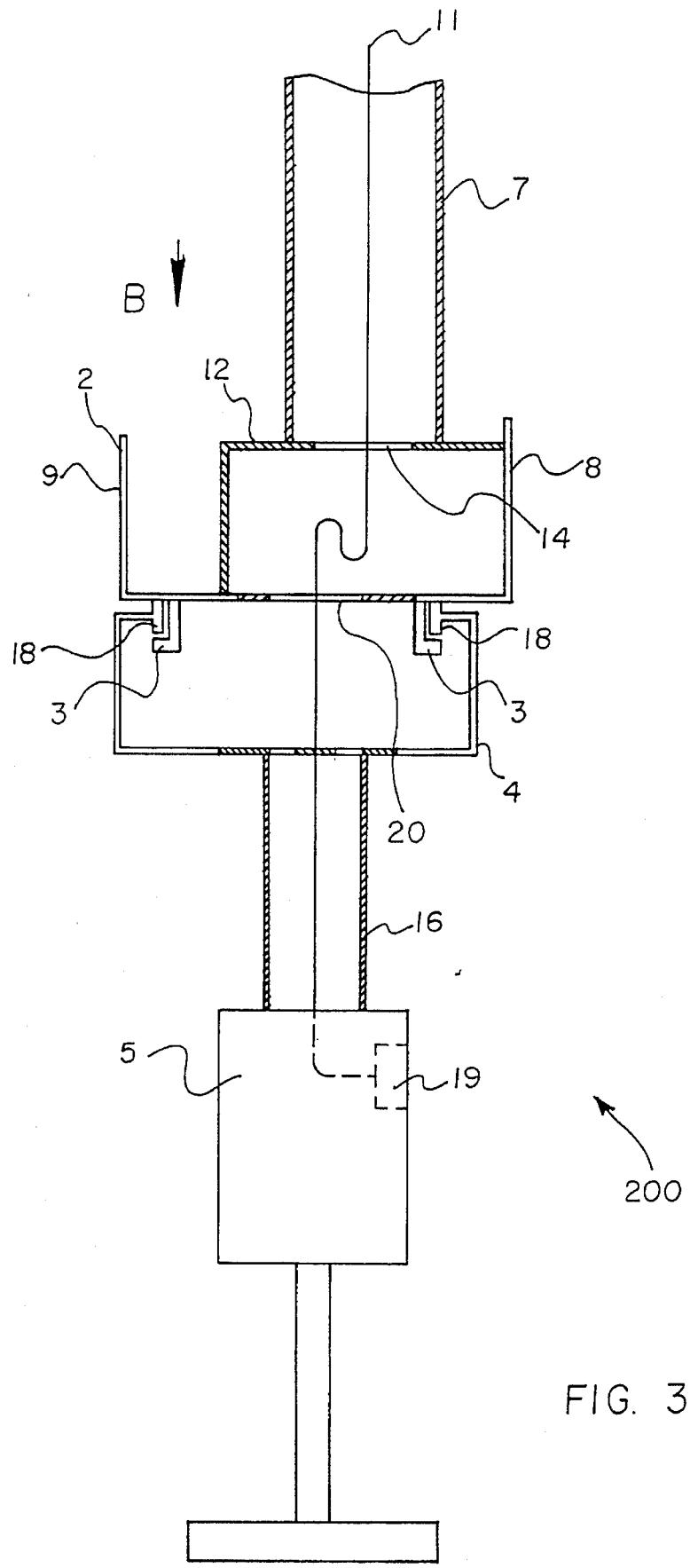
FIG. 3 is a second embodiment of supply unit in the viewing direction "A" according to FIG. 1.

FIG. 3 shows the side view of a second supply unit 200 in the same viewing direction as in FIG. 2. As a difference from the first supply unit 100, a slot-like opening 20, through which the supply lines 11 are guided, is provided as a tube guide in the underside 13 of the supply beam 2, instead of the deflecting plate 15, FIG. 2.

Figure 4:
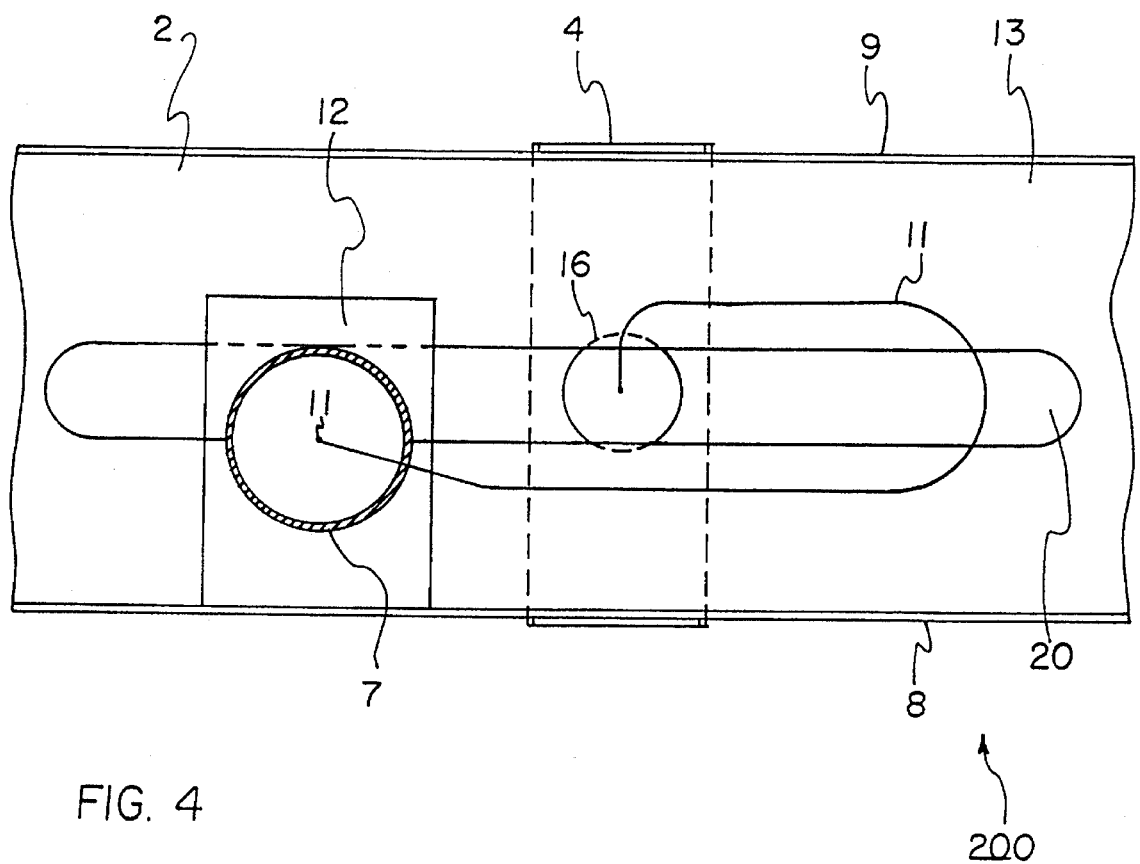
FIG. 4 is a top view of the second embodiment in the viewing direction "B" according to FIG. 3.

FIG. 4 shows a top view of the second supply unit 200 in the viewing direction "B" according to FIG. 3. Identical components are designated by the same reference numbers as in FIG. 3.

Figure 5:
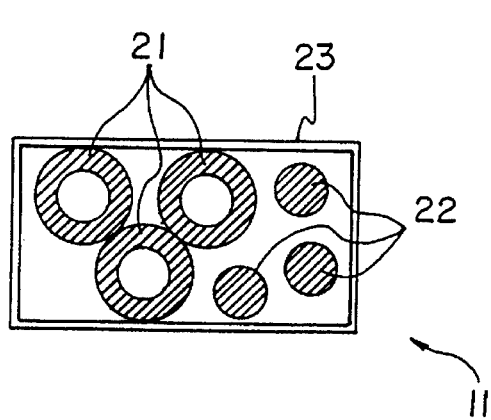
FIG. 5 is a sectional representation of the supply lines.

FIG. 5 shows a longitudinal section of the supply lines 11, which consist of lines 21 carrying medical gas and electrical lines 22 and are held together by a tube-like jacket 23. The tube-like jacket 23 may be a cable or cable drain.

While specific embodiments of the invention have been shown and described in detail to illustrate the application of the principles of the invention, it will be understood that the invention may be embodied otherwise without departing from such principles.

What is claimed is:

1. A supply unit for medical treatment instruments, comprising: a structural tube-type supply beam, said supply beam being fastened to a ceiling; electrical and medical gas-carrying supply lines extending through said tube-type supply beam; tracks extending longitudinally on said supply beam; a carriage positioned on said tracks for movement along said tracks; support means arranged on said carriage, said supply lines being freely displaceable within said supply beam and said supply lines being accommodated within said supply beam in the form of a loop including a first partial length $L_1$ and a second partial length $L_2$, a sum of said first partial length $L_1$ and said second partial length $L_2$ of said freely displaceable supply lines within said supply beam corresponding at least to a predetermined movement of said carriage along said tracks; and tube guide means for deflecting said supply lines from said supply beam to said support device.

2. A supply unit according to claim 1, wherein said supply lines lie on an underside of said supply beam.

3. A supply unit according to claim 1, wherein said supply lines are accommodated in a tube-like jacket, said tube-like jacket being disposed within said supply beam.

4. A supply unit according to claim 2, wherein said supply lines are accommodated in a tube-like jacket, said tube-like jacket being disposed within said supply beam.

5. A supply unit according to claim 3, wherein said tube-like jacket is a cable chain.

6. A supply unit according to claim 1, wherein said tube guide means includes a deflecting plate connected to one of said carriage and said support device, said deflecting plate being guided along one of a sectional front side and a sectional rear side of said supply beam.

7. A supply unit according to claim 6, wherein said deflecting plate is arranged on said sectional rear side, hidden from a user of the supply unit, said sectional front side having a height $h_1$ and sectional rear side having a height $h_2$, said height $h_2$ being smaller than said height $h_1$.

8. A supply unit according to claim 1, wherein said tube guide means includes a slot-like opening in said supply beam, said slot-opening extending along said track.

9. A supply unit according to claim 1, further comprising supply connections located on said support device, said supply lines being connected to said supply connections.

10. A supply unit for medical treatment instruments, comprising: a structural tube-type supply beam, said supply beam being fastened to a ceiling; electrical and medical gas-carrying supply lines extending through said tube-type supply beam; tracks extending longitudinally on said supply beam; a carriage positioned on said tracks for movement along said tracks; support means arranged on said carriage, said supply lines being freely displaceable within said supply beam and said supply lines being accommodated within said supply beam in the form of a first partial length $L_1$ and a second partial length $L_2$, said first partial length $L_1$ extending in a first direction of said tracks and said second partial length $L_2$ extending in a second, opposite direction of said tracks, a sum of said first partial length $L_1$ and said second partial length $L_2$ of said freely displaceable supply lines within said supply beam corresponding at least to a predetermined movement of said carriage along said tracks; and tube guide means for deflecting said supply lines from said supply beam to said support device.

* * * * *